United States Patent
Oliver et al.

(10) Patent No.: US 9,415,034 B2
(45) Date of Patent: Aug. 16, 2016

(54) INHIBITORS AND ENHANCERS OF URIDINE DIPHOSPHATE-GLUCURONOSYLTRANSFERASE 2B (UGT2B)

(75) Inventors: Yoa-Pu Hu Oliver, Taipei (TW); Cheng-Huei Hsiong, Taipei (TW); Mei-Ting Wang, Taipei (TW); Li-Heng Pao, Taipei (TW)

(73) Assignee: NATIONAL DEFENSE MEDICAL CENTER, Taipei (TW)

( * ) Notice: Subject to any disclaimer, the term of this patent is extended or adjusted under 35 U.S.C. 154(b) by 606 days.

(21) Appl. No.: 12/325,139

(22) Filed: Nov. 28, 2008

(65) Prior Publication Data
US 2009/0074708 A1    Mar. 19, 2009

Related U.S. Application Data

(63) Continuation-in-part of application No. 11/028,615, filed on Jan. 5, 2005, now abandoned.

(51) Int. Cl.
| | | |
|---|---|---|
| *A61K 31/704* | (2006.01) | |
| *A61K 31/7028* | (2006.01) | |
| *A61K 31/70* | (2006.01) | |
| *A61K 31/225* | (2006.01) | |
| *A61K 31/353* | (2006.01) | |
| *A61K 31/57* | (2006.01) | |
| *A61K 31/7048* | (2006.01) | |

(52) U.S. Cl.
CPC .......... *A61K 31/225* (2013.01); *A61K 31/353* (2013.01); *A61K 31/57* (2013.01); *A61K 31/704* (2013.01); *A61K 31/7048* (2013.01)

(58) Field of Classification Search
CPC .......... A61K 31/225; A61K 31/353; A61K 31/7048; A61K 31/704; A61K 31/57
USPC .................................. 514/27, 25; 536/4.1
See application file for complete search history.

(56) References Cited

U.S. PATENT DOCUMENTS

| | | | | |
|---|---|---|---|---|
| 4,582,835 A | * | 4/1986 | Lewis | A61K 9/0019 514/282 |
| 6,004,969 A | * | 12/1999 | Hu | 514/282 |
| 6,193,991 B1 | * | 2/2001 | Shukla | 424/426 |
| 6,444,234 B1 | * | 9/2002 | Kirby et al. | 424/725 |
| 6,677,346 B1 | * | 1/2004 | Achari et al. | 514/282 |
| 2003/0215462 A1 | * | 11/2003 | Wacher et al. | 424/195.18 |

FOREIGN PATENT DOCUMENTS

JP    2000191544 A  *  7/2000

OTHER PUBLICATIONS

Abstract of Inoue (JP 2000191544 A), Jul. 11, 2000.*
Barkhuizen et al. (The American Journal of Gastroenterology, vol. 94, No. 5, May 1, 1999, pp. 1355-1360(6).*
Bálint (Clin Rheumatol (2002) (Suppl 1): S17-S18).*
Machine English Translation of Inoue (JP 2000191544 A), Jul. 11, 2000.*
Brown et al. (Biochemical Society Transactions (1993), 21(4), 463S).*
Aungst et al (Int. J. Pharm. 33, 225-234 (1986)).*

* cited by examiner

*Primary Examiner* — Shaojia Anna Jiang
*Assistant Examiner* — Michael C Henry
(74) *Attorney, Agent, or Firm* — Chun-Ming Shih

(57) ABSTRACT

A UGT2B inhibitor capable of increasing the bio-availability of a drug, is a compound in a free base or a pharmaceutically acceptable salt form that is selected from the group consisting of: capillarisin, isorhamnetin, β-naphthoflavone, α-naphthoflavone, hesperetin, terpineol, (+)-limonene, β-myrcene, swertiamarin, eriodictyol, cineole, apigenin, baicalin, ursolic acid, isovitexin, lauryl alcohol, puerarin, trans-cinnamaldehyde, 3-phenylpropyl acetate, isoliquritigenin, paeoniflorin, gallic acid, genistein, glycyrrhizin, protocatechuic acid, ethyl myristate, umbelliferone, PEG (Polyethylene glycol) 400, PEG 2000, PEG 4000, Tween 20, Tween 60, Tween 80, BRIJ® 58, BRIJ® 76, Pluronic® F68, Pluronic® F127, and a combination thereof. A UGT2B enhancer capable of enhancing a clearance rate of morphine-like analgesic agents, is a compound in a free base or a pharmaceutically acceptable salt form that is selected from the group consisting of: nordihydroguaiaretic acid, wogonin, trans-cinnamic acid, baicalein, quercetin, daidzein, oleanolic acid, homoorientin, hesperetin, narigin, neohesperidin, (+)-epicatechin, hesperidin, liquiritin, eriodictyol, formononetin, quercitrin, genkwanin, kaempferol, isoquercitrin, (+)-catechin, naringenin, daidzin, (−)-epicatechin, luteolin-7-glucoside, ergosterol, rutin, luteolin, ethyl myristate, apigenin, 3-phenylpropyl acetate, umbelliferone, glycyrrhizin, protocatechuic acid, poncirin, isovitexin, 6-gingerol, cineole, genistein, trans-cinnamaldehyde, and a combination thereof.

2 Claims, 3 Drawing Sheets

INHIBITORS AND ENHANCERS OF URIDINE DIPHOSPHATE-GLUCURONOSYLTRANSFERASE 2B (UGT2B)

RELATED APPLICATIONS

This application is a continuation-in-part of U.S. patent application Ser. No. 11/028,615, filed on Jan. 5, 2005 now abandoned.

BACKGROUND OF THE INVENTION

1. Field of the Invention

This invention aims at enhancing drug bio-availability by providing an effective UGT2B inhibitor as well as a UGT2B enhancer for increasing the detoxification ability of individuals.

2. Description of the Prior Art

The drug metabolism process in human body, especially the metabolism of high fat-soluble drugs, includes two biotransformation steps: phase I reaction that catalyzes fat-soluble molecules to polarized molecules, and phase II reaction that produces highly polarized molecule through conjugation, such that the drugs can be metabolized efficiently and excreted to urine or feces.

The most common and important conjugation is glucuronidation by uridine diphosphate (UDP)-glucuronosyltransferases (refers to as UGTs; EC 2.4.1.17 hereafter).

The UGTs is one of the major enzymes in phase II reaction in human. It is now evident that UGTs have more than 110 isoenzymes. UGTs can catalyze the conjugation of UDP-glucuronic acid (UDPGA) and the endogenous fat-soluble compounds' chemical bonds, such as hydroxyl, sulfonyl, carboxylic acid, amine, or amide, to facilitate the O-glucuronidation, N-glucuronidation, or S-glucuronidation (King et al., 2000, Curr. Drug Metab., 1(2): 143-61), and thus enhances the polarity of the fat-soluble molecules.

According to a review article published by Radominska-Pandya et al (Drug Metab Rev. 31(4):817-99, 1999), most human UGTs belong to the UGT1A and UGT2B families. The UGT1A family consists of UGT1A1, UGT1A2P, UGT1A3-10, UGT1A11P and UGT1A12p, while UGT2B family consists of UGT2B4, UGT2B7, UGT2B10, UGT2B15 and UGT2B17.

In addition, UGTs posses extensive substrate specificity. The UGT1A and UGT2B metabolize different compounds. The UGT1A family mainly metabolizes phenolic compounds such as estrone, 2-hydroxyestrone, 4-nitrophenol, 1-naphthol, etc. with the involvement of bilirubin. The UGT2B family metabolizes steroid compounds such as androsterone, linoleic acid, etc. with the involvement of bile acids.

It was reported that UGTs can either enhance the bioactivity of some compounds or, under certain circumstances, transform some compound into toxic substances, such as morphine, steroids, bile acids and mid retinoids. (see Vore et al. (1983a) Life Sciences 32:2989-2993; Vore et al. (1983b) Drug Metabolism Reviews 14:1005-1019; Abbott and Palmour (1988) Life Sciences 43:1685-169). It was also reported that UGTs have involved in the activation of polycyclic aromatic hydrocarbons (PAH) and heterocyclic aromatic amines. (Munzel et al. (1996) Archives of Biochemistry and Biophysics, 355: 205-210; Bock et al. (1998) Advances in Enzyme Regulation, 38: 207-222).

UGTs can be found in several tissues including liver, kidney, bile duct, esophagus, stomach, intestine, rectum, ileum, jejunum, spleen, mammary gland, skin, lung, and brain. However, the distribution of various UGTs in human body differs by type. For instance, UGT2B7 exists mainly in esophagus, liver, intestine, colon, kidney, and spleen; while UGT1A1 can be found in liver, bile duct, stomach and colon (Tukey et al. (2000) Annu. Rev. Pharmacol. Toxicol., 40: 581-616. Review).

Studies by Burchell and Coughtrie (Burchell B and Coughtrie MW (1997) Environmental Health Perspectives 105: 739-747) found differences among individuals in their abilities to metabolize medicines, due to the genetic polymorphisms in UGT genes. Therefore, the information regarding the regulatory function of UGTs in individual's drug metabolism process is essential in evaluating a drug's potential pharmaceutical efficacy and its interaction with other drugs.

The UGTs is also an important detoxification system in human body. In addition to the endogenous fat-soluble compounds, the exogenous fat-soluble compounds can also become water-soluble through glucuronidation, and thus enhances the excretion of the exogenous fat-soluble compounds and maintains human body's normal detoxification function.

Therefore, the glucuronidation will be hampered by defected UGTs activities in individuals who suffered from liver diseases. Consequently, the liver's lower clearance rate in metabolizing drug will increase the toxic reaction and the rate of carcinogenesis in an individual with liver diseases.

According to literatures, butylated hydroxyanisole (BHA) (Buetler et al. (1995) Toxicology & Applied Pharmacology 135(1): 45-57) and pregnenolone-16α-carbonitrile (PCN) (Viollon-Abadie et al., 1999, Toxicology & Applied Pharmacology., 155(1):1-12) may activate UGT2B.

Before circulating through the entire body, most drugs that are absorbable to gastroenterological tract will enter the liver through portal circulation. This is the so-called "first-pass effect". It had been confirmed that the ubiquitous UGTs in the intestine and the liver is one of the major enzymes that are necessary to the "first-pass effect" of the drug absorbance process. Such "first-pass effect" will stabilize a drug's bio-availability.

Owing to this phenomenon, the pharmacological scientists are aggressively looking for safe, effective, and reversible UGT inhibitors to apply to drugs with low bio-availability due to their fast metabolism, for the purpose of increasing their efficacy. Such a need is especially evident in oral medicines.

Studies in UGT inhibitors and their interactions with drugs have been conducted in recent year. Reported UGT inhibitors include silymarin (Venkataramanan et al. 2000, Drug Metabolism and Disposition 28: 1270-1273), quinoline (Dong et al., 1999, Drug Metabolism & Disposition 27:1423-1428), oltipraz (Vargas et al., 1998, Drug Metabolism & Disposition 26:91-97), tacrolimus (Zucker et al., 1999, Therapeutic Drug Monitoring 21:35-43), octyl gallate, apigenin, imipramine, clozapine, acetaminophen, and emodin (Radominska-Pandya et al., 1999, as mentioned earlier).

It was also reported that diazepam and flunitrazepam (FM2) can strongly inhibit the activity of UGT2B (Grancharov et al., 2001, harmacol Ther., 89(2):171-86).

Since the aforementioned UGT inhibitors are active drug ingredients by themselves and will induce prominent physical responses, they are not good candidates as drug absorption enhancers.

It was well recognized among those who are familiar with the techniques that a good UGT inhibitor for enhancing the bio-availability of drugs should at least posses the following three characteristics: (1) No or minimum pharmacological effect, except inhibiting UGT; (2) The inhibition should be reversible. In other words, UGTs should be able to restore its normal functions, after the inhibitors were excreted or metabolized; and (3) The efficacy of the inhibitor should be able to prominently lower the activity of UGTs in the intestine and the liver with a minimum dose.

It was known in recent years that grapefruit juice and certain components of other natural products, such as narigin, naringenin, hesperidine and other flavonoids, can inhibit some pharmacological activities.

US 6,121,23 depicts that by using essential oil, one can enhance the bio-availability of an oral medicine in the intestine of a mammal. The method involves co-administration of a therapeutic dose of the pharmaceutical compound and an essential oil or a component of essential oil where 10% inhibition was demonstrated with the presence of no more than 0.01 wt. of essential oil or a component of essential oil. In this US patent, it was also demonstrated that essential oil enhances the bio-availability of the drug through its inhibition of cytochrome P450.

Another study indicated that flavonoids compounds prepared from the liver of Long-Evants rat, such as naringenin, hesperetin, kaempferol, quercetin, rutin, flavone, α-naphthoflavone, and β-naphthoflavone can inhibit the metabolism of estrone and estradiol in microsomes (Zhu et al. 1998, J Steroid Biochem Mol Biol, 64(3-4): 207-15).

According to Chinese herbal medicine literature, due to its relatively milder toxicity than synthetic compounds, Chinese herbal enhancers (CHEs) were widely used in about 30%-75% of Chinese herbal medicine prescriptions. According to Japan's Food and Drug Administration, among 210 official Chinese herbal compound prescriptions, *Glycyrrhizae radix* is the most frequently used CHE (in 150 or 71.4% prescriptions), followed by *Zingiberis* (in 42.9% prescriptions) and *Zizyphi fructus* (in 31.9% prescriptions). In the Japanese National Formulary (2nd Edition), the most frequently used CHEs are *Glycyrrhizae radix* (71.4%), *Zingiberis* (42.9%), Holen (poria) (35.2%), *Paeoniae radix* (32.9%), *Zizyphi fructus* (31.9%) and *Cinnamami cortex* (29.5%).

Other than these frequently used CHEs, studies regarding other CHEs are rare. For the purpose of developing new UGT inhibitors, further investigations on some other CHEs are worthwhile. For instance, flavonoids-containing CHEs like *Scutellariae radix* (contains baicalin, wogonin, baicalein, skullcap-flavon I and wogoin glucuronide), *Artemisiae cpillaris herba* (contains capillarisin, cirsilineol, cirsimaritin, genkwanin, rhamrcocitrin); and terpenoids-containing CHEs like *Alismatis rhizome* (contains alisol monoacetate and triterpenoids), Moutan radicis cortex (contains paeoniflorin, oxypaeoniflorin and its benzoyl derivatives), Aconiti tuber (contains aconitine, mesaconitine, jesaconitine and atisine), *Tragacantha* (contains tragoside I and tragoside II), Persical semen (contains 24-methylenecycloartanol), Cimicifugae rhizome (contains cimigenol, cimigenol xyloside and its 12-hydroxyl derivatives and dahurinol).

Possible mechanisms of CHEs as enhancers of drug absorption include: (1) catalysts: new active ingredients may be derived from the cooking or the preparation process of Chinese herbal medicine; (2) carrier: carrying the drug's active ingredients going through barriers to reach its targets; (3) enzyme inhibitor: take UGT inhibitor as an example, if a drug's active ingredients cannot be absorbed by oral administration due to UGT metabolism, it may become orally absorbable by combining with a CHEs that lowers or restricts the "first-pass effect".

This application's inventor found that glycyrrhizin in *Glycyrrhizae radix* and oleanolic acid and β-myrcene in *Zizyphi fructus* can enhance the partition coefficient in drugs like acyclovir, buprenorphine, or buprenorphine and hence increase these drug's transdermal permeation more than 1,000 percent in either in vitro or clinical trials. Reference: Dr. Oliver Yoa-Pu Hu's acyclovir Patent (Taiwan Patent No. 084682, U.S. Pat. No. 6,162,459, Japan Patent No. 2681881); buprenorphine Patent (Taiwan Patent No. 137835, U.S. Pat. No. 6,004,969); and piroxicam Patent (Taiwan Patent No. 133855).

New opioids drugs such as buprenorphine, nalbuphine and butorphanol were developed recently. They are classified as narcotic agonist-antagonist analgesics, due to their dual agonistic and antagonistic effects on opioids-receptors (Schmidt, W. K. et al, Drug Alcohol Depend. 14, 339, 1985). In addition to having high affinity to opioids-receptors, these dual-effect drugs can also be used as an antagonist to compensate for the drawbacks of narcotic analgesics, such as to lower their addictive effect and to drastically minimize their respiratory inhibition.

According to Schmidt et al (1985), nalbuphine possesses both the affinity to Kappa receptor (OP2) and the antagonist effect to Mu receptor (OP3). There is no obvious addiction or synergistic effect with only a slight respiratory inhibition, after a six-month continuous usage of nalbuphine. Therefore, in clinical trials, nalbuphine is safer than the traditional narcotic analgesics, and has exhibited an excellent therapeutic effect.

The drawback of this drug is its poor absorbability when delivered orally. In Goodman and Gillman's study, the bio-availability of nalbuphine is 11±4%, while the bio-availability of nalbuphine in animal is 2.7±0.4%, a shorter half-life. In current clinical pharmacology, the drug can only be administered through IV, not orally. The nalbuphine's pharmacokinetic studies indicate its half life through the excretion of liver is 5 hours, and about 7% of the drug are excreted to the urine in its original form (Birgit et al. 1996, Drug metabolism and Disposition, 25(1):1-4; Birgit et al. 1998, Drug Metabolism and Disposition, 26(1):73-77; and Richard et al. 1990, Clin. Pharmacol Ther., 47:12-19).

Published literature has proved that nalbuphine is mainly metabolized through UGT2B7 (Radominska-Pandya et al., 1999).

U.S. Pat. No. 6,004,969 depicts a transdermal delivery of buprenorphine. The method includes the delivery of a drug to patients that contains the following pharmaceutical ingredients: 1) about 0.8% of buprenorphine or its HCl salt; 2) about 10-20% of one or a combination of the following drug enhancers: 2-pinene, trans-cinnamic acid, β-myrcene or β-myrcene; and 3) about 79.2-89.2% of one or a combination of the following inert ingredients: stearyl alcohol, sodium carboxymethyl-cellulose, glycerol, cetyl alcohol, 1,3-propylene glycol, and water.

Studies regarding the use of Chinese herbal medicine in diseases treatment and prevention have become prominent in recent years. However, the issues about what are the herbal medicines that can inhibit UGT and how to apply them to the UGT-related therapeutic usages are still need to be addressed.

Besides, there are a lot of studies indicate that many pharmaceutical excipients might have effect on the activity of cytochrome P450. It is thought generally that most of the excipients are used to increase the volume, the solubility or stability and so on of drugs. However, such point of view might need to be changed.

Mountfield et al. (Mountfield et al., 2000) indicates at 2000 that some of the excipients influence CYP3A4 enzyme activity in microsomal enzyme experiment in vitro. Some other excipients are also reported in other researches, for example, PEG400 (Johnson et al., 2003), Cremophor RH40 (Wabdel et al., 2003) both have effect on the enzyme activity of CYP3A4.

Bravo et al. (Bravo et al., 2003) have studied the effect of surfactant on activity of enzyme. The medicine studied is colchicine that is metabolized by P-gp and CYP3A4 in vivo. The control group is colchicine dissolved in 0.9% NaCl solution, and the experimental group is colchicine dissolved in 5% solutol HS15-NaCl solution. The result shows that the concentration of experimental group is above two times of controlled group. The clearing rate of experimental group is obviously two folds lower than controlled group. And in-vitro hepatocyte experiment shows that 0.003% solutol HS15 inhibits clearing rate of colchicine. It is worth noted that this kind of surfactants are thought to destroy cell membrane in other studies, affect metabolism of cell (Silva et al., 2004), change the usage of co-factor in catalysis reaction of enzymes or interaction between substrate and enzyme. However, there is no evidence showing that solutol HS15 at such concentration has any impact on the intact of the cell under light microscope. Therefore, the detailed mechanism needs to be investigated in the future.

Generally speaking, the research and development of new medicine could be divided into several stages: New Chemical Entity (NCE), pre-clinical toxicity testing, pharmacological testing and finally, the clinical testing. Traditional chemical selection is to modify the structure on those who has pharmacological activity or extract the biological chemicals from plants. Unfortunately, most of these chemicals are fat-soluble compound, thus, different excipients are added to improve solubility and stability of these chemicals. For pharmaceutical industry, it is inevitable to use excipient. Hence, this invention not only studies the effect of using CHEs as UGT inhibitor and enhancer, but also the effect of excipients on enzyme activity of UGT in order to provide more UGT inhibitors and enhancers that are safe and effective.

In sum, the development of a safe, effective and reversible UGT inhibitor will enable the oral administration of high "first-pass effect" drugs, and will minimize the side effect and the dosage of highly variable drugs. In addition, the toxicity of the carcinogenic compounds caused by UGT activities can also be reduced.

Developing a safe, efficient and reversible UGT enhancer is also a desirable goal of the pharmaceutical industry. It will help patients with low clearance rate in drug metabolism due to reduced liver functions to metabolize the drugs, and enhance the detoxification function of the liver.

SUMMARY OF THE INVENTION

First of all, this invention provides a UGT2B inhibitor that can increase the bio-availability of morphine-like analgesic agents. This inhibitor is a compound in a free base or a pharmaceutically acceptable salt form that is selected from the group consisting of: capillarisin, isorhamnetin, β-naphthoflavone, α-naphthoflavone, hesperetin, terpineol, (+)-limonene, β-myrcene, swertiamarin, eriodictyol, cineole, apigenin, baicalin, ursolic acid, isovitexin, lauryl alcohol, puerarin, trans-cinnamaldehyde, 3-phenylpropyl acetate, isoliquiritigenin, paeoniflorin, gallic acid, genistein, glycyrrhizin, protocatechuic acid, ethyl myristate, umbelliferone, PEG (Polyethylene glycol) 400, PEG 2000, PEG 4000, Tween 20, Tween 60, Tween 80, BRIJ® 58, BRIJ® 76, Pluronic® F68, Pluronic® F127, and a combination thereof.

This invention also provides a pharmaceutical composition that includes the aforementioned UGT2B inhibitor as its active ingredient, a pharmaceutically effective amount of morphine-like analgesic agents and a pharmaceutically acceptable inert ingredient. The pharmaceutical composition in this invention can decrease the enzymatic activity of UGT2B, and thus increase the bio-availability of analgesics such as morphine.

Secondly, this invention provides an UGT2B enhancer that can enhance the clearance rate of morphine-like analgesic agents. This enhancer is a compound with a free base or a pharmaceutically acceptable salt comprises of selected materials from the following: nordihydroguaiaretic acid, wogonin, trans-cinnamic acid, baicalein, quercetin, daidzein, oleanolic acid, homoorientin, hesperetin, narigin, neohesperidin, (+)-epicatechin, hesperidin, liquiritin, eriodictyol, formononetin, quercitrin, genkwanin, kaempferol, isoquercitrin, (+)-catechin, naringenin, daidzin, (−)-epicatechin, uteolin-7-glucoside, ergosterol, rutin, luteolin, ethyl myristate, apigenin, 3-phenylpropyl acetate, umbelliferone, glycyrrhizin, protocatechuic acid, poncirin, isovitexin, 6-gingerol, cineole, genistein, trans-cinnamaldehyde, and a combination thereof.

This invention also provides a pharmaceutical composition that includes the aforementioned UGT2B enhancer as its active ingredient, a pharmaceutically effective amount of morphine-like analgesic agents and a pharmaceutically acceptable inert ingredient. The pharmaceutical composition in this invention can increase the enzymatic activity of UGT2B, and thus increase the clearance rate of morphine-like analgesic agents.

These features and advantages of the present invention will be fully understood and appreciated from the following detailed description of the accompanying figures.

DETAILED DESCRIPTION OF THE PREFERRED EMBODIMENT

Figure 1:
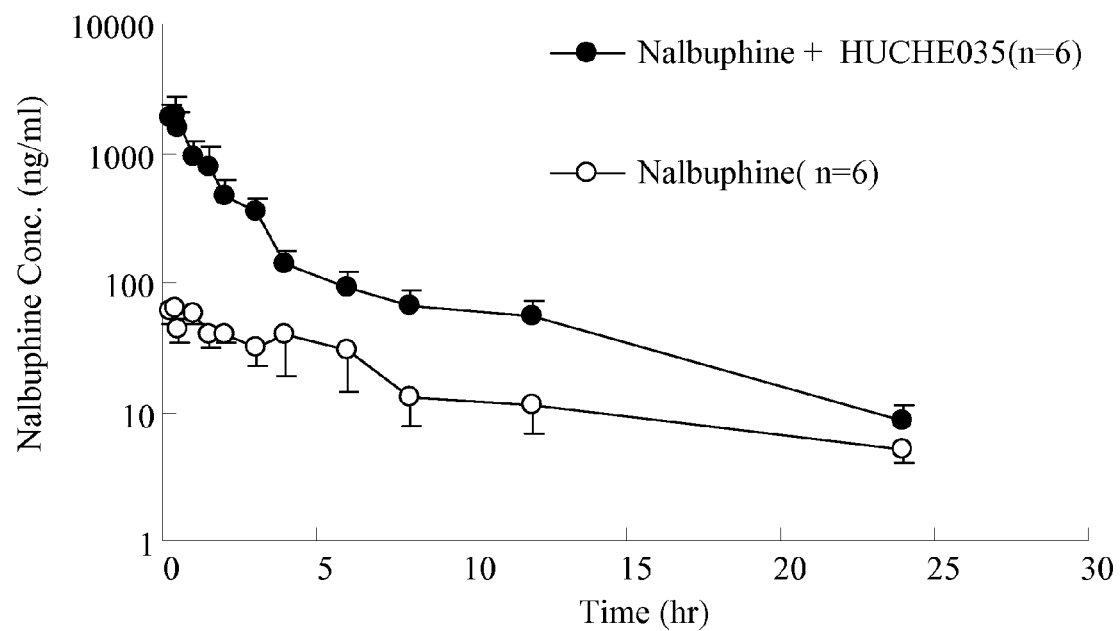
FIG. 1 depicts the temporal effect of capillarisin on the concentration of nalbuphine in blood, after the SD rats were orally treated with nalbuphine.
Figure 1:
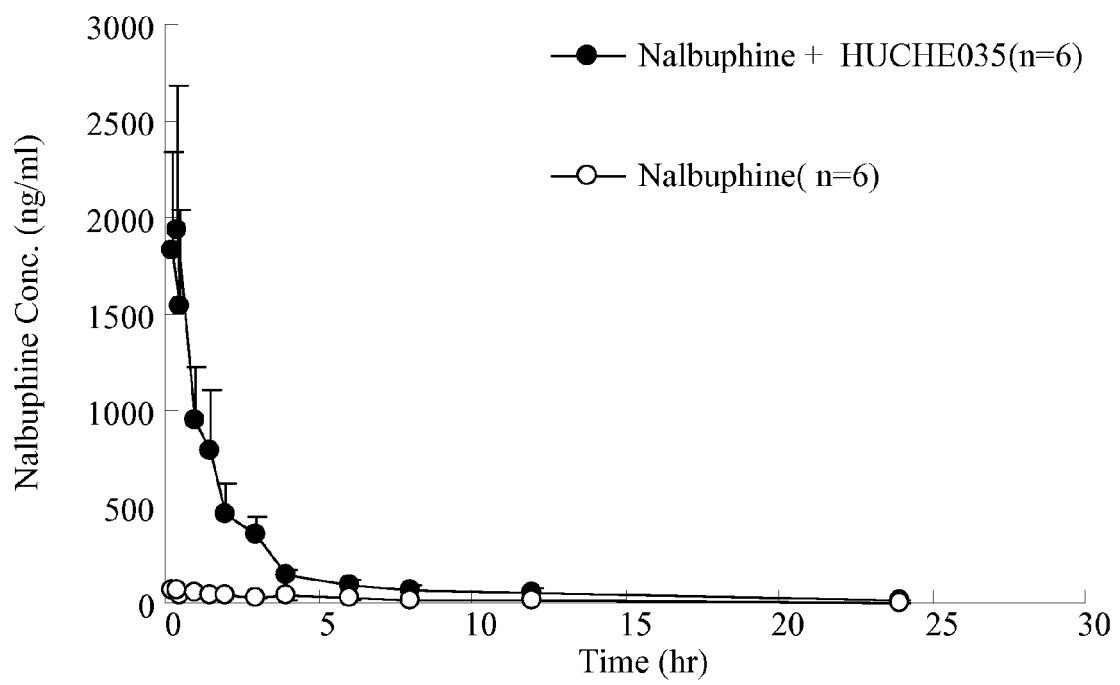

In the first dimension, this invention provides a UGT2B inhibitor that is a compound in a free base or a pharmaceutically acceptable salt form that is selected from the group consisting of: capillarisin, isorhamnetin, β-naphthoflavone, α-naphthoflavone, hesperetin, terpineol, (+)-limonene, β-myrcene, swertiamarin, eriodictyol, cineole, apigenin, baicalin, ursolic acid, isovitexin, lauryl alcohol, puerarin, trans-cinnamaldehyde, 3-phenylpropyl acetate, isoliquiritigenin, paeoniflorin, gallic acid, genistein, glycyrrhizin, protocatechuic acid, ethyl myristate, umbelliferone, PEG (Polyethylene glycol) 400, PEG 2000, PEG 4000, Tween 20, Tween 60, Tween 80, BRIJ® 58, BRIJ® 76, Pluronic® F68, Pluronic® F127, and a combination thereof.

In a good example of this invention, the UGT2B inhibitor is a compound in a free base or a pharmaceutically acceptable salt form that is selected from the group consisting of: capillarisin, isorhamnetin, β-naphthoflavone, α-naphthoflavone, hesperetin, terpineol, (+)-limonene, β-myrcene, swertiamarin and eriodictyol; or a combination of them. In a better example, the UGT2B inhibitor contains capillarisin.

It was confirmed that UGT2B inhibitor of this invention can increase the bio-availability of a drug. The applicability of UGT2B inhibitor in the preparation of pharmaceutical compositions, especially the morphine analgesics, is also predicted in this invention.

Therefore, this invention provides a pharmaceutical composition which contains:
(a) a pharmacologically active ingredient of aforementioned UGT2B inhibitor, and
(b) a pharmaceutically effective amount of morphine-like analgesic agents, and
(c) a pharmaceutically acceptable inert ingredient.

In the second dimension, this invention provides an UGT2B enhancer that is a compound in a free base or a pharmaceutically acceptable salt form that is selected from the group consisting of: nordihydroguaiaretic acid, wogonin, trans-cinnamic acid, baicalein, quercetin, daidzein, oleanolic acid, homoorientin, hesperetin, narigin, neohesperidin, (+)-epicatechin, hesperidin, liquiritin, eriodictyol, formononetin, quercitrin, genkwanin, kaempferol, isoquercitrin, (+)-catechin, naringenin, daidzin, (−)-epicatechin, uteolin-7-glucoside, egosterol, rutin, luteolin, ethyl myristate, apigenin, 3-phenylpropyl acetate, umbelliferone, glycyrrhizin, protocatechuic acid, poncirin, isovitexin, 6-gingerol, cineole, genistein, trans-cinnamaldehyde, and a combination thereof.

In a good example of this invention, the UGT2B enhancer is a compound in a free base or a pharmaceutically acceptable salt form that is selected from the group consisting of: nordihydroguaiaretic acid, wogonin, trans-cinnamic acid, baicalein, quercetin, daidzein, oleanolic acid, homoorientin, hesperetin, narigin, neohesperidin, (+)-epicatechin, hesperidin, liquiritin and eriodictyol. A better example of UGT2B enhancer contains nordihydroguaiaretic acid.

It was confirmed that the UGT2B enhancer of this invention can increase the clearance rate of a drug. The applicability of the UGT2B enhancer in the preparation of pharmaceutical compositions, especially the morphine analgesics, is also predicted in this invention.

Therefore, this invention provides a pharmaceutical composition which contains:
(a) a pharmacologically active ingredient of aforementioned UGT2B enhancer, and
(b) a pharmaceutically effective amount of morphine-like analgesic agents, and
(c) a pharmaceutically acceptable inert ingredient.

This invention also provide a method to improve the oral bioavailability of morphine-like analgesic agents, where the said method is orally coadministered morphine-like analgesic agents with Uridine diphosphate (UDP)-glucuronosyltransferases 2B (UGT2B) inhibitor that is a compound in a free base form or a pharmaceutically acceptable salt form that is selected from the group of: capillarisin, isorhamnetin, β-naphthoflavone, α-naphthoflavone, hesperetin, (+)-limonene, swertiamarin, eriodictyol, apigenin, baicalin, ursolic acid, isovitexin, lauryl alcohol, puerarin, 3-phenylpropyl acetate, isoliquritigenin, paeoniflorin, gallic acid, genistein, glycyrrhizin, protocatechuic acid, ethyl myristate, umbelliferone, PEG (Polyethylene glycol) 400, PEG 2000, PEG 4000, Tween 20, Tween 60, Tween 80, BRIJ® 58, BRIJ® 76, Pluronic® F68, Pluronic® F127, terpineol, β-myrcene, cineole, and trans-cinnamaldehye to human subjects; and where the said morphine-like agents are a combination of the following: (−)-morphine, naloxone, nalorphine, oxymorphone, hydromorphone, dihydromorphone, codeine, naltrexone, nalbuphine and buprenorphine.

The UGT2B inhibitor or enhancer used in this invention is easily obtainable to persons familiar with the technology. It can be chemically synthesized in the laboratory, purchased from chemical company, or purified from pertinent natural sources. The UGT2B inhibitor or enhancer used in the following experimental examples are purchased from Sigma Chemical Co., Nacalai Tesque (Kyoto, Japan) and Indofine Chemical Co., Inc. (Somerville, N.J.).

In this invention, the term "pharmacologically active ingredient" refers to a pharmaceutical composition that can either inhibit or enhance the UGT2B activity when a proper quantity was used in therapeutic purposes. The proper quantity of this active ingredient varies by type of disease, patient's weight, age, health condition, and the way the drug was delivered. It should be determined by technically qualified persons.

In this invention, the term "pharmaceutically acceptable" means that the salt component of an UGT2B inhibitor or enhancer must be compatible with other ingredients of the pharmaceutical composition, and will not hamper the application of this composition onto an individual.

The pharmaceutical composition of this invention can be used exclusively on an individual or in combination with morphine-like analgesic agents.

In a good example of this invention, the morphine-like analgesic agents include: (−)-morphine, naloxone, nalorphine, oxymorphone, hydromorphone, dihydromorphine, codeine, naltrexone, naltrindole, nalbuphine, and buprenorphine. In a better example, the morphine-like analgesic is nalbuphine.

The pharmaceutical composition of this invention can be manufactured as an intravenously- or orally-administered substance.

The pharmaceutical composition of this invention can be manufactured in a form for intravenous administration with the addition of sterile water or non-water solution, dispersion, suspension or emulsion, and sterile powder that can be reconstituted to sterile solution for injection. Examples of suitable water or non-water inert ingredients, diluents, solvents, or carriers include: water, alcohol, propylene glycol, polyethylene glycol, glycerol, or other similar compounds, and organic ester such as ethyl oleate.

It is better that the pharmaceutical composition of this invention be manufactured in a form that can be administered orally. The oral forms include solid substances (e.g., capsule, tablet, powder, and granule) and liquid substance (e.g., emulsion, solution, dispersion, suspension).

In addition, the pharmaceutical composition of this invention and other drugs can be presented in different forms. For example, it can be delivered as a tablet, by injection, or as an oral syrup. Furthermore, it is noteworthy that the pharmaceutical composition of this invention can be administered with other drugs at the same time or sequentially. For instance, as a tablet, it can be concentrated in a single tablet or spread to several tablets and can be given simultaneously or sequentially. All combinations, delivery methods and sequences can be flexibly administered by persons who are familiar with these techniques.

The dose and frequency in delivering the pharmaceutical composition of this invention varies according to: the severity of the illness to be treated, route of delivery, and the patient's weight, age, physical condition and the response. In general, the dosage of the pharmaceutical composition of this invention is estimated to fall in the range of 0.01 mg/Kg weight to 20 mg/Kg, as a single dose or several doses, and can be delivered through a non-gastroenterological or oral route.

A detailed description of better examples

The following experiments further describe the invention in detail. Please be advised that these experiments are examples. They are not the limitations of this invention's applications.

EXPERIMENT 1 in vitro Experiment of UGT2B Inhibitor

Material and Method:
1. The Preparation of UGT2B Inhibitor

In the following experiment, 27 different kinds of CHEs and 10 different excipients were used as UGT2B inhibitor in this invention. These CHEs are pure compounds available commercially, and were purchased from Sigma Chemical Co., Nacalai Tesque (Kyoto, Japan) and Indofine Chemical Co., Inc. (Somerville, N.J.). Their category, name, source and chemical formula are listed in Table 1. These UGT2B inhibitors are dissolved in alcohol at the concentration of 1, 10, 100 µM for the following experiment.

Besides, these excipients are commercially available pure compounds, they are PEG (Polyethylene glycol) 400, PEG 2000, PEG 4000, Tween 20, Tween 60, Tween 80, BRIJ® 58, BRIJ® 76, Pluronic® F68, Pluronic® F127. These excipients are dissolved in water and make up to 0.5%, 5%, 50% (wt %, w/v) for the following experiment. (Note: BRIJ is a registered trademark of ICI Americas, Inc.; Pluronic is a registered trademark of BASF Corporation.)

TABLE 1

| | | | |
|---|---|---|---|
| | | The category, name, source and chemical formula of UGT2B inhibitors | |
| Category | Name | Source (Scientific name) | Chemical formula and molecular weight |
| Flavonoid | Apigenin | *Chamomillae flos* | 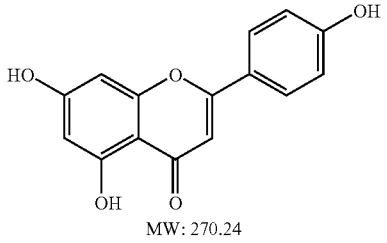 [SMILES: O=c1cc(-c2ccc(O)cc2)oc2cc(O)cc(O)c12] MW: 270.24 |
| | Isovitexin | *Swertiae herba* | 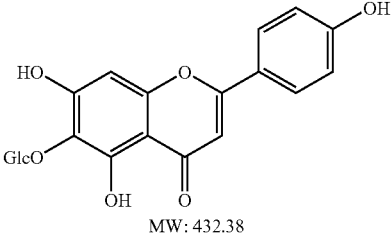 MW: 432.38 |
| | Isorhamnetin | *Sennae folium* | 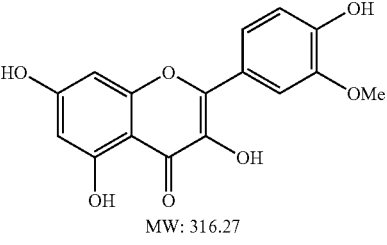 [SMILES: COc1cc(-c2oc3cc(O)cc(O)c3c(=O)c2O)ccc1O] MW: 316.27 |
| | Umbelliferone | *Aurantii fructus immaturus* | 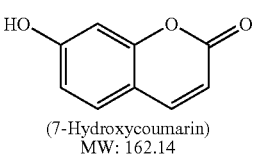 (7-Hydroxycoumarin) MW: 162.14 |

TABLE 1-continued
The category, name, source and chemical formula of UGT2B inhibitors
| Category | Name | Source (Scientific name) | Chemical formula and molecular weight |
|---|---|---|---|
| | Diosmin | — | 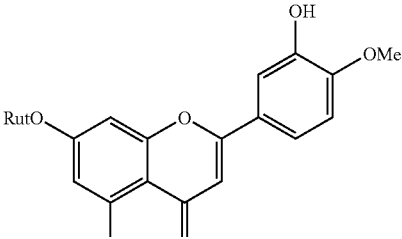 MW: 608.55 |
| | Hesperetin | *Citri reticulatae* | 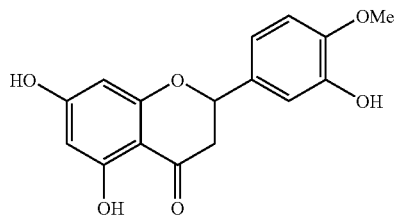 MW: 302.28 |
| | baicalin | *Scutellariae radix* | 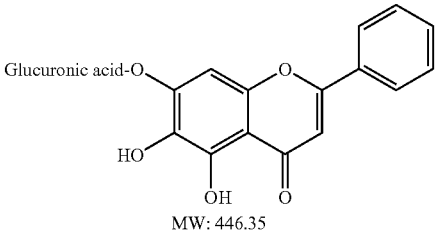 MW: 446.35 |
| | Puerarin | *Puerariae radix* | 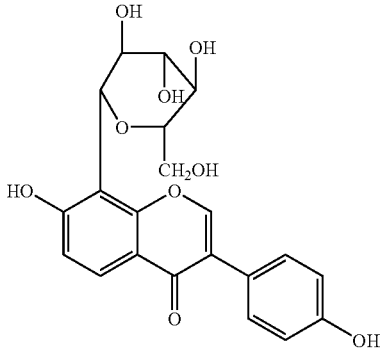 MW: 416.38 |
| | Capillarisin | *Artemisiae capillaris herba* | 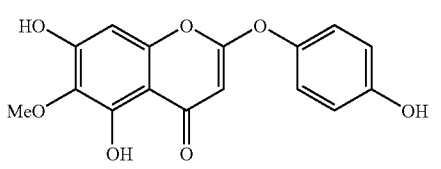 MW: 316.27 |

TABLE 1-continued

The category, name, source and chemical formula of UGT2B inhibitors

| Category | Name | Source (Scientific name) | Chemical formula and molecular weight |
|---|---|---|---|
| | Genistein | *Puerariae radix* | 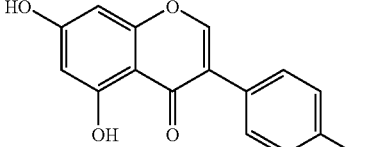<br>MW: 270.24 |
| | α-Naphthoflavone | — | 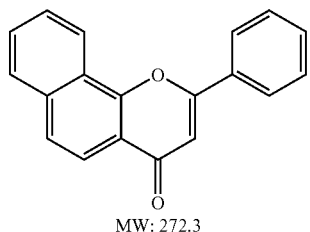 [SMILES: O=c1cc(-c2ccccc2)oc2c1ccc1ccccc12]<br>MW: 272.3 |
| | β-Naphthoflavone | — | 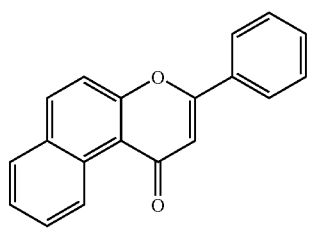<br>MW: 272.3 |
| | Eriodictyol | *Cinnamami cortex* | 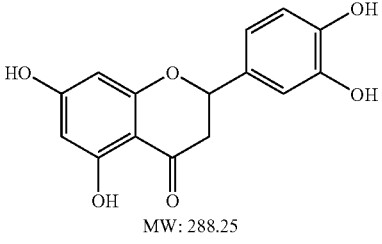 [SMILES: O=C1CC(c2ccc(O)c(O)c2)Oc2cc(O)cc(O)c21]<br>MW: 288.25 |
| essential oil | 3-Phenylpropyl Acetate | *Cinnamami cortex* | 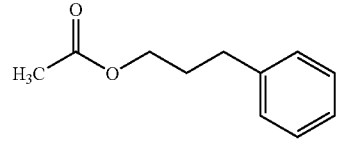<br>MW: 178.23 |
| | Trans-Cinnamaldehyde | *Cinnamami cortex* | 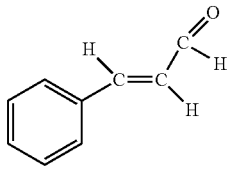<br>MW: 132.16 |

TABLE 1-continued

The category, name, source and chemical formula of UGT2B inhibitors

| Category | Name | Source (Scientific name) | Chemical formula and molecular weight |
|---|---|---|---|
| | β-Myrcene | *Amome cardamomi fructus* | 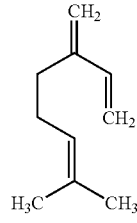 MW: 136.23 |
| | Terpineol | *Cinae flos(Santonica)* | 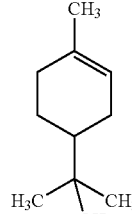 MW: 154.25 |
| | (+)-Limonene | *Cardamomi fructus* | 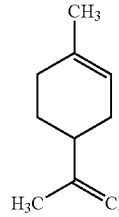 MW: 136.23 |
| | Ethyl Myristate | *Myristicae semen* | |
| | Cineole | *Cinae flos(Santonica)* | 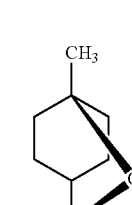 MW: 154.25 |
| Tennins | Paeoniflorin | *Paeoniae radix* | 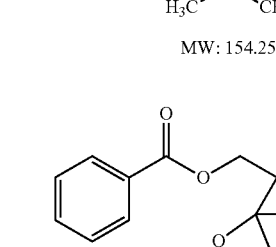 MW: 480.47 |

TABLE 1-continued
The category, name, source and chemical formula of UGT2B inhibitors
| Category | Name | Source (Scientific name) | Chemical formula and molecular weight |
|---|---|---|---|
| | Swertiamarin | *Swertiae herba* | 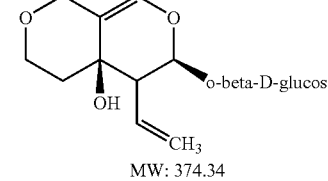<br>MW: 374.34 |
| chalcon | Isoliquritigenin | *Astragali radix* | 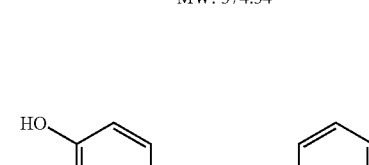<br>MW: 256.25 |
| Saponin | Glycyrrhizin | *Glycyrrhizae radix* | 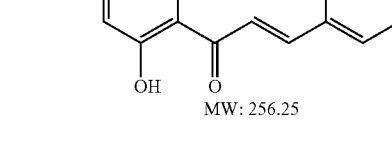<br>MW: 822.94 |
| | Ursolic Acid | *Zizyphi fructus* | <br>MW: 456.70 |

TABLE 1-continued

The category, name, source and chemical formula of UGT2B inhibitors

| Category | Name | Source (Scientific name) | Chemical formula and molecular weight |
|---|---|---|---|
| — | Protocatechuic acid | *Cinnamami cortex* | 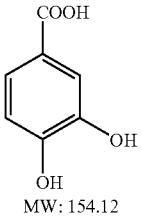 [SMILES: O=C(O)c1ccc(O)c(O)c1] MW: 154.12 |
| — | Gallic Acid | — | 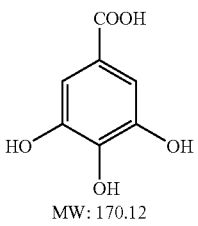 [SMILES: O=C(O)c1cc(O)c(O)c(O)c1] MW: 170.12 |
| — | Lauryl Alcohol | | 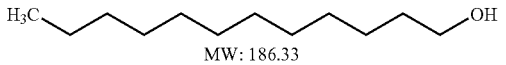 MW: 186.33 |

2. The Preparation of Liver Microsome

The Sprague-Dawley male rats, weighted 300-400 g are used as model animals in these experiments. The microsome is prepared as follows:

i. Sacrifice a rat after 12-16 hours fasting, take its liver; wipe dry the liver and weigh it.
ii. Add 300% (by volume) of cold 0.3M sucrose solution, and homogenize the liver.
iii. Centrifuge the homogenized liver suspension at 9000×g speed (KS-800, Kubota, made in Japan) for 10 min at 4° C. Collect the supernatant.
iv. Centrifuge the supernatant at 105,000×g speed (L8-60M, Beckman, made in USA) for 60 min at 4° C.
v. Remove the supernatant, add 0.3M sucrose (of the same volume) and repeat the homogenization. The homogenized liver suspension is the microsome. Store the microsome at −70° C.

Thaw the microsome before use. Add 5 μl/ml BRIJ®35 (Fisher et al. 2000, Drug Metabolism & Disposition. 28(5): 560-6) into microsome by a ratio of microsome:BRIJ®35=8:1 (v/v).

[note BRIJ® 35 SOLUTION 30% W/V, BRIJ is a registered trademark of ICI Americas, Inc.]

3. Measure the Protein Amount in Microsome

The protein amount is determined as follows:

i. Take 0.1 ml microsome and dilute to 5 ml 0.85% NaCl (50-fold dilution, v/v). Take 0.2 ml of the diluted microsome and place it in a capped test tube (triple experiments). Separately, replacing microsome with 0.2 ml NaCl as the control.
ii. Add 2.2 ml Biuret regent (SIGMA, 690-A) into each test tube, mix well and store at room temperature for 10 min.
iii. Add 0.1 ml folin regent (SIGMA, 690-A), mix immediately, and store at room temperature for 30 min. Measure the absorbance at 550 nm wave length within the 30 min.

Measure the concentration of protein in microsome based on the standard curve generated by various bovine albumin concentration and absorbance.

4. The Measurement of the Inhibition of UGT2B Activity in vitro i. (A) solution: 17 μl 1M Tris-HCl buffer, 17 μl 50 mM $MgCl_2$, 40 μl microsome and 10 μl 150 mM UDPGA solution.
   (B) solution: mix 20 mM nalbuphine solution with the inhibitor to be tested at the 1:1 ratio.
ii. Mix solution (A) and 17 μl solution (B) thoroughly, place in a 37° C. water bath and shake at 125 rpm for 60 min.
iii. Add 1 ml ACN to interrupt the reaction.
iv. Centrifuge at 130,000×g speed at 4° C. for 5 min, and
v. Take 150 μl supernatant and analyze the concentration of nalbuphine in a high performance liquid chromatography (HPLC).

5. The Measurement of Nalbuphine Concentration (1) Condition of HPLC

The mobile phase consists of 15% sodium acetate (5 mM/L, pH 3) and 85% ACN with a 1.0 ml/min flow rate. Set the spectrophotometer's (RF-551, Shimadzu, Kyoto, made in Japan) excitation wave length at 210 nm and emission wave length at 345 nm. Set the Ultra-violet detector's (SPD-10A, Shimadzu, Kyoto, made in Japan) wave length to 210 nm.

(2) Prepare the Standard Solution

Prepare nalbuphine solution at 0.5, 1, 2.5, 5, 10, 15, 18, 20 mM concentrations. Resolve the standard solution in water, but dilute the solution with alcohol if it contains inhibitor.

Use the same protocol as described in step 4 (The measurement of the inhibition of UGT2B activity in vitro), except that the de-ionized water, instead of the "150 mM UDPGA solution" be used in the (A) solution.

After HPLC analysis, obtain a corrected curve by plotting HPLC reading of nalbuphine wave heights against its relative concentration. Analyze the standard deviation (SD), coefficient of variance (% CV), and % error to examine the accuracy.

Results:

The result is displayed in Table 2. Capillarisin has the best inhibitory effect on the metabolism of nalbuphine in microsome. The inhibition rate could reach 111.077 (21.807) %. Other CHEs including isorhamnetin, β-naphthoflavone, α-naphthoflavone, hesperetin, terpineol, (+)-limonene, β-myrcene, swertiamarin, and eriodictyol also have at least 30% inhibition rate.

TABLE 2

The effect of the inhibitor on the metabolism of nalbuphine in liver microsome

| | % Inhibition (Mean ± SD) | | |
|---|---|---|---|
| Name | 8.5 μM | 85 μM | 850 μM |
| apigenin | −26.668 ± 13.062 | 53.998 ± 15.763 | −16.067 ± 17.864 |
| isovitexin | 29.821 ± 9.786 | −5.528 ± 9.096 | −12.377 ± 8.912 |
| isorhamnetin | 88.419 ± 11.605 | 85.132 ± 14.703 | 106.846 ± 8.102 |
| umbelliferone | −14.707 ± 5.810 | 4.596 ± 8.236 | −20.590 ± 18.244 |
| hesperetin | 51.736 ± 21.691 | −59.096 ± 18.879 | −124.34 ± 49.356 |
| baicalin | 36.298 ± 9.403 | 46.253 ± 22.923 | 44.262 ± 2.879 |
| puerarin | 3.919 ± 5.607 | 18.289 ± 7.685 | 10.103 ± 5.841 |
| capillarisin | 111.077 ± 21.807 | 105.410 ± 21.808 | 105.257 ± 19.306 |
| genistein | 15.630 ± 6.046 | 5.733 ± 6.406 | −9.200 ± 5.182 |
| α-naphthoflavone | 72.33 ± 2.811 | 97.79 ± 4.370 | 90.81 ± 7.175 |
| β-naphthoflavone | 95.82 ± 5.461 | 86.02 ± 16.487 | 99.72 ± 15.877 |
| eriodictyol | −1.061 ± 3.714 | −17.133 ± 2.297 | 14.114 ± 2.878 |
| 3-phenylpropyl acetate | −26.288 ± 27.337 | 17.280 ± 5.837 | 2.390 ± 22.463 |
| trans-cinnamaldehyde | −6.973 ± 3.782 | −3.099 ± 9.457 | 18.284 ± 10.350 |
| β-myrcene | 16.812 ± 1.716 | 35.290 ± 0.220 | 34.883 ± 7.296 |
| terpineol | 40.558 ± 6.511 | 62.367 ± 2.582 | 58.164 ± 4.241 |
| (+)-limonene | 18.284 ± 0.793 | 45.284 ± 7.844 | 44.238 ± 2.284 |
| ethyl myristate | −27.845 ± 14.692 | −12.134 ± 5.706 | 6.326 ± 1.484 |
| cineole | −8.413 ± 18.562 | −12.107 ± 6.679 | 58.890 ± 8.558 |
| paeoniflorin | 12.093 ± 8.544 | 17.797 ± 9.248 | −2.966 ± 9.529 |
| swertiamarin | 28.239 ± 2.248 | 27.930 ± 4.129 | −2.499 ± 6.899 |
| isoliquiritigenin | −2.482 ± 5.506 | 17.592 ± 4.565 | 18.637 ± 16.623 |
| glycyrrhizin | 9.926 ± 6.659 | −20.298 ± 3.674 | −5.653 ± 6.620 |
| ursolic acid | 34.171 ± 18.576 | 17.267 ± 14.316 | 6.482 ± 18.840 |
| protocatechuic acid | −20.210 ± 5.957 | −4.563 ± 3.372 | 9.844 ± 1.872 |
| gallic acid | 15.842 ± 4.418 | 8.051 ± 3.024 | 12.223 ± 4.080 |
| lauryl alcohol | 14.422 ± 3.370 | 19.496 ± 3.464 | 6.232 ± 6.752 |

Besides, Table 3 and 4 depict the result about the excipients in the experiment above. PEG 4000 has the best inhibitory effect on the metabolism of nalbuphine in microsome, the inhibitory rate reaches 108.222 (±3.356) %; the best inhibitory rate of the other excipients reach 60% at least.

TABLE 3

The effect of the excipient on the metabolism of nalbuphine in liver microsome-1

| Name | % Inhibition (Mean ± SD) | | |
|---|---|---|---|
| Concentration of excipients (wt %, w/v) | 0.0425% | 0.425% | 4.25% |
| PEG 400 | 102.137 ± 6.156 | 97.030 ± 12.875 | 93.359 ± 10.893 |
| PEG 2000 | 32.615 ± 5.192 | 86.635 ± 7.948 | 97.011 ± 4.588 |
| PEG 4000 | 71.410 ± 3.109 | 108.222 ± 3.356 | 107.329 ± 6.242 |
| Tween 20 | 83.734 ± 6.465 | 99.863 ± 8.487 | 93.926 ± 7.862 |
| Tween 60 | 78.475 ± 4.915 | 30.917 ± 7.429 | 27.327 ± 9.644 |
| Tween 80 | 91.163 ± 5.861 | 92.387 ± 6.302 | 99.651 ± 3.344 |

TABLE 4

The effect of the excipient on the metabolism of nalbuphine in liver microsome-2

| Name | % Inhibition (Mean ± SD) | | |
|---|---|---|---|
| Concentration of excipient (wt %, w/v) | 0.02125% | 0.2125% | 2.125% |
| BRIJ ® 58 | 78.117 ± 6.634 | 41.592 ± 5.606 | −33.648 ± 11.873 |

TABLE 4-continued

The effect of the excipient on the metabolism of nalbuphine in liver microsome-2

| Name | % Inhibition (Mean ± SD) | | |
|---|---|---|---|
| BRIJ ® 76 | 40.488 ± 2.327 | 29.959 ± 2.572 | 60.439 ± 7.751 |
| Pluronic ® F68 | 97.431 ± 5.764 | 98.925 ± 4.475 | 65.768 ± 2.371 |
| Pluronic ® F127 | 14.499 ± 28.385 | 70.247 ± 36.296 | 83.845 ± 16.451 |

EXPERIMENT 2 in vitro Experiment of UGT2B Enhancer

This experiment uses the same protocol described in Experiment 1, except by testing the 40 CHEs listed in Table 5 as the UGT2B enhancer. Those CHEs are commercially available pure compounds, acquired from Sigma Chemical Co., Nacalai Tesque (Kyoto, Japan) and Indole Chemical Co. Inc (Somerville, N.J.). Their categories, names, sources, and chemical compositions are described in Table 5.

TABLE 5
Category, name, source, and chemical composition of the UGT2B enhancers.
| Category | Name | Source (scientific name) | Chemical formula and molecular weight |
|---|---|---|---|
| Flavonoid | Genikwanin | *Artemisiae cpillaris herba* | 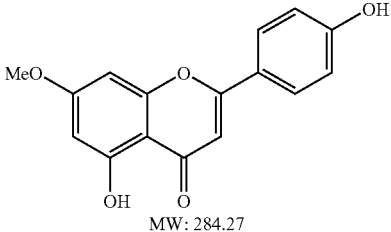 [SMILES: COc1cc(O)c2c(=O)cc(-c3ccc(O)cc3)oc2c1] MW: 284.27 |
| | Apigenin | *Chamomillae flos* | 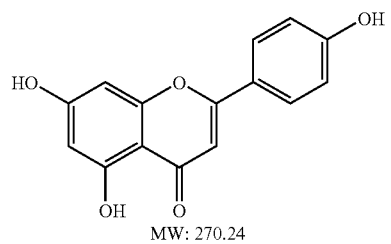 [SMILES: O=c1cc(-c2ccc(O)cc2)oc2cc(O)cc(O)c12] MW: 270.24 |
| | Luteolin | *Digitals folium* | 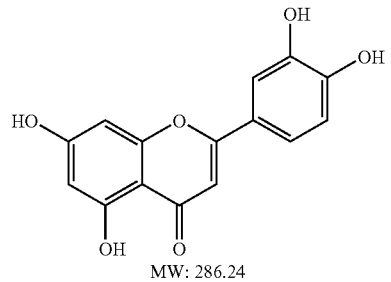 [SMILES: O=c1cc(-c2ccc(O)c(O)c2)oc2cc(O)cc(O)c12] MW: 286.24 |
| | Luteolin-7-Glucoside | *Digitals folium* | 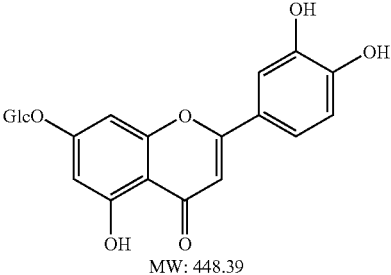 MW: 448.39 |
| | Homoorientin | *Swertiae herba* | 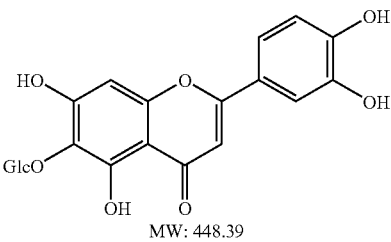 MW: 448.39 |

TABLE 5-continued

Category, name, source, and chemical composition of the UGT2B enhancers.

| Category | Name | Source (scientific name) | Chemical formula and molecular weight |
|---|---|---|---|
| | Isovitexin | *Swertiae herba* | 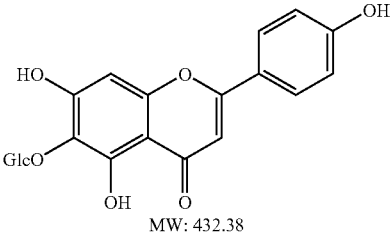 MW: 432.38 |
| | Neohesperidin | *Aurantii fructus immaturus* | 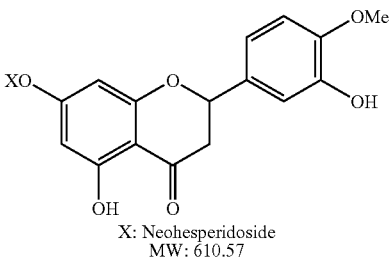 X: Neohesperidoside MW: 610.57 |
| | Formononetin | *Astragali radix* | 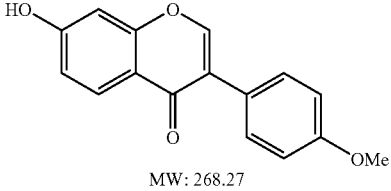 [SMILES: COc1ccc(-c2coc3cc(O)ccc3c2=O)cc1] MW: 268.27 |
| | Kaempferol | *Sennae folium* | 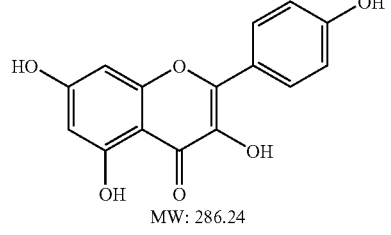 MW: 286.24 |
| | Isoquercitrin | *Hydrangeae dulcis folium* | 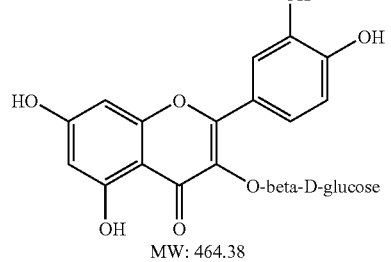 MW: 464.38 |
| | 6-Gingerol | *Zingiberis* | 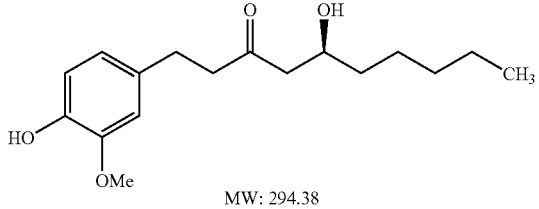 [SMILES: CCCCC[C@H](O)CC(=O)CCc1ccc(O)c(OC)c1] MW: 294.38 |

TABLE 5-continued

Category, name, source, and chemical composition of the UGT2B enhancers.

| Category | Name | Source (scientific name) | Chemical formula and molecular weight |
|---|---|---|---|
| | Liquiritin | *Glycyrrizae radix* | 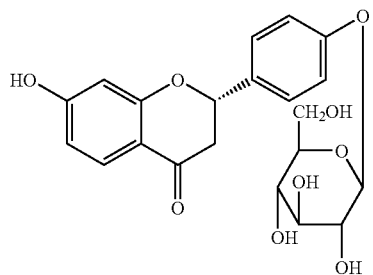 MW: |
| | naringenin | *Aurantii fructus immaturus* | 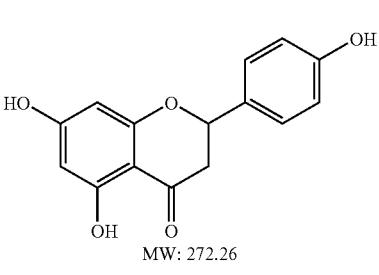 MW: 272.26 |
| | Umbelliferone | *Aurantii fructus immaturus* | 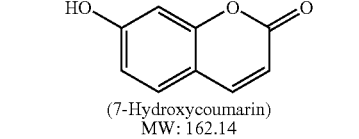 (7-Hydroxycoumarin) MW: 162.14 |
| | Rutin | *Sophorae flos* | 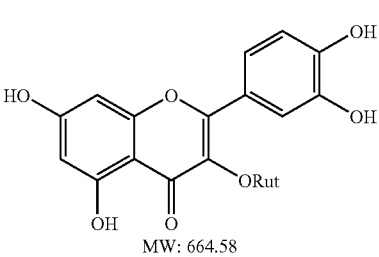 MW: 664.58 |
| | Hesperidin | *Aurantii fructus immaturus* | 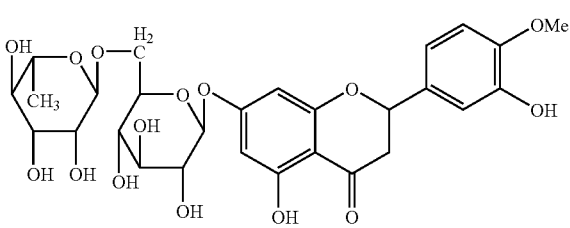 MW: 610.57 |
| | Diosmin | — | 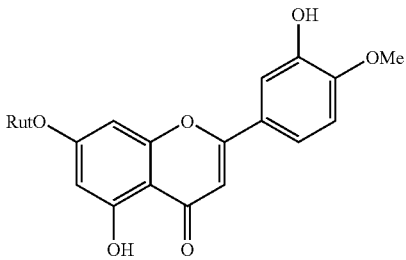 MW: 608.55 |

TABLE 5-continued

Category, name, source, and chemical composition of the UGT2B enhancers.

| Category | Name | Source (scientific name) | Chemical formula and molecular weight |
|---|---|---|---|
| | Hesperetin | *Citri reticulatae* | 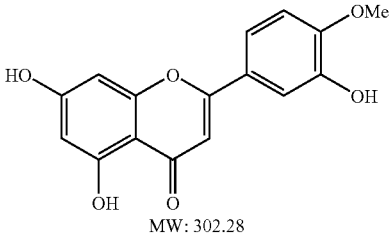 [SMILES: COc1ccc(-c2cc(=O)c3c(O)cc(O)cc3o2)cc1O]<br>MW: 302.28 |
| | Wogonin | *Scutellariae radix* | 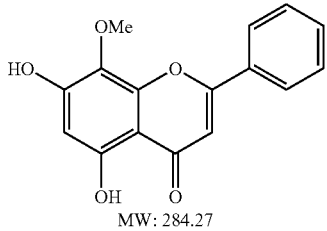 [SMILES: COc1c(O)cc(O)c2c(=O)cc(-c3ccccc3)oc12]<br>MW: 284.27 |
| | Baicalcin | *Scutellariae radix* | 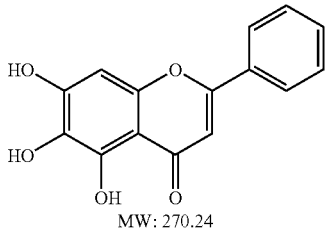 [SMILES: O=c1cc(-c2ccccc2)oc2cc(O)c(O)c(O)c12]<br>MW: 270.24 |
| | Daidzein | *Puerariae radix* | 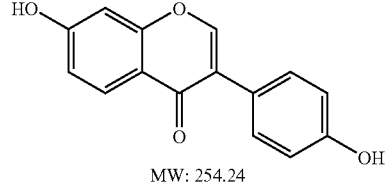 [SMILES: O=c1c(-c2ccc(O)cc2)coc2cc(O)ccc12]<br>MW: 254.24 |
| | Daidzin | *Puerariae radix* | 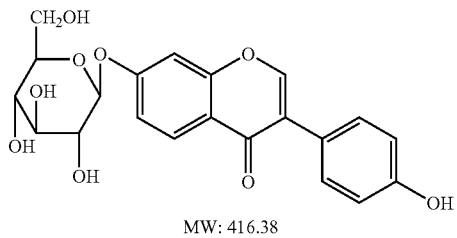<br>MW: 416.38 |
| | Quercitrin | *Viscum coloratum* | 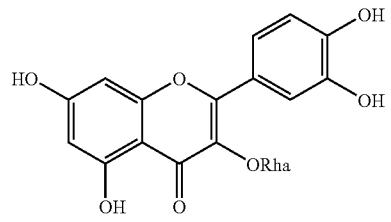<br>MW: 448.38 |

TABLE 5-continued

Category, name, source, and chemical composition of the UGT2B enhancers.

| Category | Name | Source (scientific name) | Chemical formula and molecular weight |
|---|---|---|---|
| | Quercetin | *Viscum coloratum* | 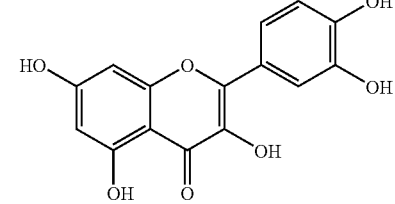<br>MW: 302.2 |
| | Nordihydroguaiaretic acid | — | 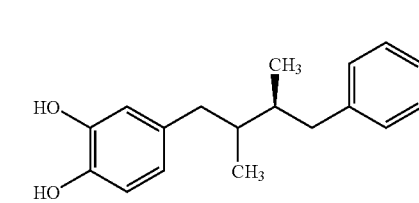<br>MW: 302.36 |
| | Genistein | *Puerariae radix* | 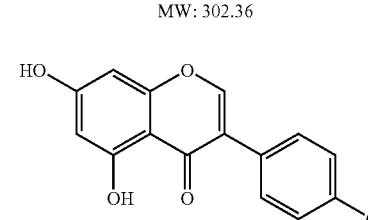<br>MW: 270.24 |
| | Poncirin | *Aurantii fructus immaturus* | 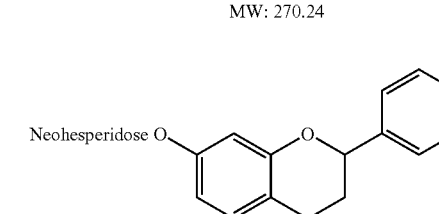<br>MW: 594.37 |
| | Narigin | *Aurantii fructus immaturus* | 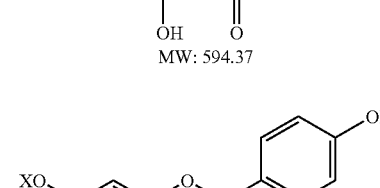<br>X: Rhamnoglucoside<br>MW: 580.54 |
| | Eriodictyol | *Cinnamami cortex* | 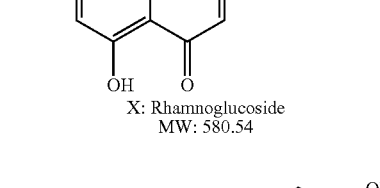<br>MW: 288.25 |

TABLE 5-continued

Category, name, source, and chemical composition of the UGT2B enhancers.

| Category | Name | Source (scientific name) | Chemical formula and molecular weight |
|---|---|---|---|
| essential oil | 3-Phenylpropyl Acetate | *Cinnamami cortex* | MW: 178.23 |
| | Trans-Cinnamaldehyde | *Cinnamami cortex* | MW: 132.16 |
| | Ethyl Myristate | *Myristicae semen* | |
| | Cineole | *Cinae flos(Santonica)* | MW: 154.25 |
| Tennins | (+)-Epicatechin | *Gambir* | MW: 290.27 |
| | (+)-Catechin | *Paeoniae radix* | MW: 290.27 |
| | (−)-Epicatechin | *Gambir* | MW: 290.27 |

TABLE 5-continued
Category, name, source, and chemical composition of the UGT2B enhancers.
| Category | Name | Source (scientific name) | Chemical formula and molecular weight |
|---|---|---|---|
| Sterol | Ergosterol | *Holen(poria)* | 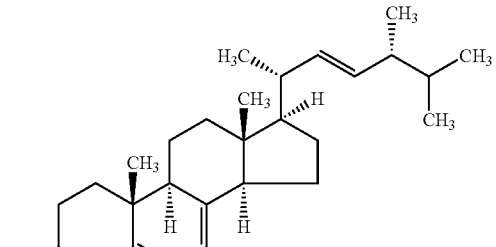 MW: 396.65 |
| Saponin | Glycyrrhizin | *Glycyrrhizae radix* | 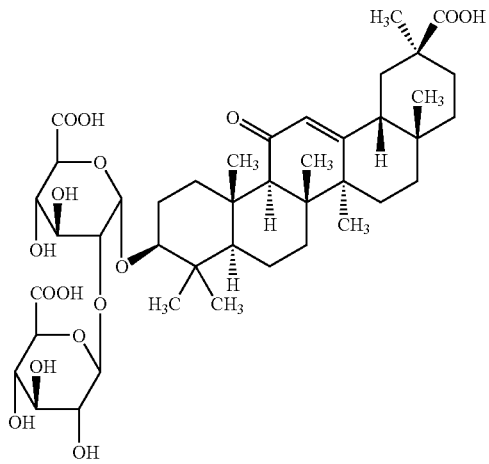 MW: 822.94 |
| Triterpenoid | Oleanolic Acid | *Zizyphi fructus* | 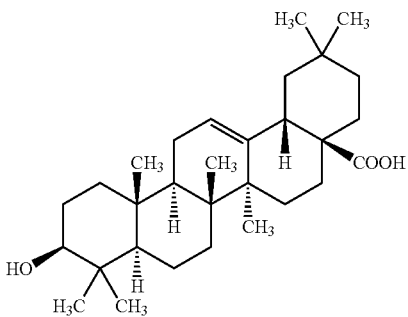 MW: 456.70 |
| — | Protocatechuic acid | *Cinnamami cortex* | 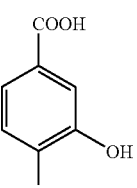 MW: 154.12 |

TABLE 5-continued

Category, name, source, and chemical composition of the UGT2B enhancers.

| Category | Name | Source (scientific name) | Chemical formula and molecular weight |
|---|---|---|---|
| — | Trans-Cinnamic Acid | — | MW: 148.16 |

Result:

The results are summarized in Table 6. The nordihydroguaiaretic acid exhibited the best enhancement effect on the metabolism of nalbuphine in liver microsome. It could reach a −188.09(±16.566) % rate of inhibition. The other CHEs including wogonin, trans-cinnamic acid, baicalein, quercetin, daidzein, oleanolic acid, homoorientin, hesperetin, narigin, neohesperidin, (+)-epicatechin, hesperidin, liquiritin, eriodictyol could have at least 30% enhancement rate.

TABLE 6

The effect of the enhancers on the metabolism of nalbuphine in liver microsome

| Enhancer | % Inhibition (Mean ± SD) | | |
|---|---|---|---|
| | 8.5 µM | 85 µM | 850 µM |
| genkwanin | −26.999 ± 4.509 | −77.684 ± 20.682 | −43.231 ± 18.793 |
| apigenin | −26.668 ± 13.062 | 53.998 ± 15.763 | −16.067 ± 17.864 |
| luteolin | −25.508 ± 26.594 | −28.324 ± 15.205 | −17.558 ± 12.135 |
| luteolin-7-glucoside | −45.053 ± 3.583 | −36.109 ± 9.203 | −47.869 ± 26.599 |
| homoorientin | −128.53 ± 27.613 | −127.21 ± 28.005 | −133.17 ± 26.968 |
| isovitexin | 29.821 ± 9.786 | −5.528 ± 9.096 | −12.377 ± 8.912 |
| neohesperidin | −66.586 ± 9.614 | −113.63 ± 8.986 | −113.46 ± 16.721 |
| formononetin | −86.463 ± 3.490 | −31.471 ± 4.775 | −24.680 ± 4.417 |
| kaempferol | −19.545 ± 14.198 | −76.028 ± 27.291 | −71.058 ± 4.509 |
| isoquercitrin | −8.089 ± 2.404 | −19.119 ± 21.887 | −71.696 ± 20.468 |
| 6-gingerol | −14.156 ± 4.469 | −13.378 ± 3.967 | −12.341 ± 1.579 |
| liquiritin | −9.382 ± 1.803 | −17.704 ± 8.510 | −29.167 ± 2.737 |
| 6-gingerol | −62.872 ± 41.065 | −48.35 ± 13.179 | −22.61 ± 14.532 |
| umbelliferone | −14.707 ± 5.810 | 4.596 ± 8.236 | −20.590 ± 18.244 |
| rutin | −19.854 ± 19.742 | −29.414 ± 29.485 | −33.458 ± 13.373 |
| hesperidin | 2.163 ± 2.725 | −31.997 ± 10.339 | −42.02 ± 4.245 |
| hesperetin | 51.736 ± 21.691 | −59.096 ± 18.879 | −124.34 ± 49.356 |
| wogonin | −128.63 ± 8.286 | −153.23 ± 6.491 | −135.55 ± 2.879 |
| baicalein | −99.628 ± 12.832 | −125.44 ± 8.620 | −145.76 ± 8.474 (212.5 µM) |
| daidzein | −127.64 ± 20.806 | −138.29 ± 4.617 | −138.40 ± 2.307 (425 µM) |
| daidzin | −29.524 ± 21.990 | −41.466 ± 16.977 | −61.04 ± 21.066 |
| quercitrin | −81.27 ± 15.027 | −83.60 ± 27.446 | −55.57 ± 12.151 |
| quercetin | −81.440 ± 5.593 | −142.98 ± 18.532 | −119.26 ± 19.351 |
| nordihydroguaiaretic acid | −142.15 ± 41.001 | −165.04 ± 22.961 | −188.09 ± 16.566 |
| genistein | 15.630 ± 6.046 | 5.733 ± 6.406 | −9.200 ± 5.182 |
| poncirin | −16.068 ± 8.122 | −8.448 ± 8.261 | −7.098 ± 18.196 |
| narigin | −124.10 ± 16.541 | −80.70 ± 4.927 | −98.15 ± 5.276 |
| 3-phenylpropyl acetate | −26.288 ± 27.337 | 17.280 ± 5.837 | 2.390 ± 22.463 |
| trans-cinnamaldehyde | −6.973 ± 3.782 | −3.099 ± 9.457 | 18.284 ± 10.350 |
| ethyl myristate | −27.845 ± 14.692 | −12.134 ± 5.706 | 6.326 ± 1.484 |
| cineole | −8.413 ± 18.562 | −12.107 ± 6.679 | 58.890 ± 8.558 |
| (+)-epicatechin | −32.553 ± 1.578 | −47.075 ± 0.533 | −8.118 ± 1.256 |
| (+)-catechin | −68.387 ± 7.344 | −54.783 ± 9.381 | −65.261 ± 47.038 |
| (−)-epicatechin | −28.68 ± 17.634 | −23.53 ± 27.304 | −48.35 ± 39.354 |
| ergosterol | −12.501 ± 28.884 | −28.311 ± 20.311 | −34.561 ± 19.877 |
| glycyrrhizin | 9.926 ± 6.659 | −20.298 ± 3.674 | −5.653 ± 6.620 |
| oleanolic acid | −87.200 ± 24.408 | −135.54 ± 15.185 | −128.64 ± 22.066 |
| protocatechuic acid | −20.210 ± 5.957 | −4.563 ± 3.372 | 9.844 ± 1.872 |
| eriodictyol | −1.061 ± 3.714 | −17.133 ± 2.297 | 14.114 ± 2.878 |
| trans-cinnamic acid | −153.03 ± 24.865 | −109.06 ± 18.574 | −134.74 ± 3.90 |

EXPERIMENT 3

The Effect of UGT2B Inhibitors on the Concentration of Nalbuphine Taken Orally

Material and Methods:
1. Experimental Animal

Healthy male Sprague-Dawley rat, weight 500-600 g, acquired from National Laboratory Animal Breeding and Research Center in Taiwan, are used. After the acquisition, the animals are kept in a room with constant temperature (at 25±1° C.), humidity and day light (12 hours per day) for one week. Before the experiment, the animals are fasted for 12-16 hours. The drugs are administered orally.

2. Preparation of UGT2B Inhibitor and Nalbuphine Solution

Standard solution of nalbuphine is dissolved in water, and all inhibitors are dissolved in alcohol.

3. Methods:
i. Anesthetize the rat with 3~5 mg/100 g body weight of pentobarbital intraperitoneally (I.P.). The rat will be anesthetized in about 20~30 min.
ii. Insert the PE-50 catheter tube into external jugular vein to sample the blood.
iii. Orally administered 6 rats with UGT2B inhibitor—capillarisin (4 mg/Kg body weight) and nalbuphine solution (100 mg/Kg body weight). Use another 6 rats as the control. They were given only nalbuphine solution (100 mg/Kg body weight). Take 0.3 mL blood sample at the 0.25, 0.5, 0.75, 1, 1.5, 2, 3, 4, 6, 8, 12 and 24 hours after treated with these drugs, centrifuge at 10000 rpm, and take 0.1 mL serum for an analysis of the concentration of nalbuphine.

4. Measurement of the Concentration of Nalbuphine
(1) Sample Preparation

Place 0.1 mL serum in a 10 mL test tube and quickly transfer it to an ice bath. Add 50 µL internal standard (buprenorphine 5 μg/mL) and 0.5 mL sodium carbonate buffer (0.5 mole/L, pH=9.25) and mixed well. Extract the serum with 4 mL n-hexane and isoamyl alcohol mixture (9:1 (v/v)), and shake for 20 min. Centrifuge at 1,080×g speed at 4° C. for 15 min, then place it in a −80° C. freezer until the water layer froze. Transfer the organic solvent layer into another clean test tube, lyophylized until dried. Add 100 μL ACN to dissolve the dried material, auto-pipette 50 μL and applied to HPLC for analyzing the concentration.

(2) Condition for HPLC Analysis

Moving phase consists of 15% sodium acetate buffer (5 mM/L, pH=3.75) and 85% ACN, with flow rate of 1.3 mL per min, an electrical chemical detector (ECD (electrochemical detector), Coulochem II, ESA) is used for the detection (E1=200 mv, E2=400 mv, E=500 mv).

(3) Preparation of the Standard Solution

The Nalbuphine that was dissolved in ACN was diluted to the concentration of 5, 10, 20, 50, 100, 200, 500, 1000, 2000, and 3000 ng/mL with serum.

Prepare the standard solution of various concentrations according to protocols described in step (1) "sample preparation". After HPLC analysis, obtain a corrected curve by plotting HPLC reading of nalbuphine wave heights against its relative concentration. Analyze the standard deviation (SD), coefficient of variance (% CV), and % error to examine the accuracy.

Result:

Table 7 shows the changes of nalbuphine in the blood from a pharmacokinetic point of view. There are significantly different Tmax, AUC, Cmax, CL/F, and V/F between the experimental and control sets. As shown in Table 7, the Tmax is 25±5 min and Cmax is 2582.3±906.6 ng/ml in SD rat after being administered with both 100 mg/Kg nalbuphine and 4 mg/Kg capillarisin orally. In comparison, the Tmax is 97±36 min and Cmax is 79.31±18 ng/ml in the control group which was treated with 100 mg/Kg nalbuphine only.

The above results indicated that due to the inhibitive effect of capillarisin on UGT2B, the adsorption of nalbuphine had a 30-fold increase from the original concentration that was orally administered; and the absolute bio-availability increased to 108% from the original 5%.

On the other hand, no significant difference in MRT, k, t1/2 value was observed between the sample and the control. It indicates the administration of capillarisin has no influence on the metabolism of nalbuphine.

FIG. 1 shows the temporal effect of capillarisin on the blood nalbuphine concentration after SD rats were given nalbuphine orally. According to FIG. 1, the concentration of serum nalbuphine in the experimental set was 32.68 times higher than in the control set, at 0.25 hour after administration. The difference in the nalbuphine concentration diminishes by time.

TABLE 7

Pharmacokinetic analysis of orally administered nalbuphine in the control set (without capillarisin) and experimental set (with capillarisin)

| PK Parameters | (unit) | Control (n = 6) Nalbuphine (Mean ± SE) | Experiment (n = 6) Nalbuphine + capillarisin (Mean ± SE) |
|---|---|---|---|
| Cmax | (ng/mL) | 79 ± 18 | 2582 ± 906* |
| Tmax | (min) | 97 ± 36 | 25 ± 5 |
| AUC(0-t) | (min * ng/mL) | 21430 ± 8823 | 218248 ± 67598** |
| AUC(total) | (min * ng/mL) | 24356 ± 8865 | 244071 ± 69510* |
| k | (1/min) | 0.0027 ± 0.0007 | 0.0027 ± 0.0006 |
| t½ | (min) | 332 ± 62 | 310 ± 59 |
| MRT | (min) | 496 ± 90 | 316 ± 103 |
| CL/F | (mL/min/kg) | 5838 ± 1049 | 826 ± 364** |
| V/F | (mL/kg) | 2919123 ± 863250 | 377412 ± 170431* |

Note:
*indicates < 0.05;
**indicates $p \leq 0.01$

EXPERIMENT 4

Effects of UGT2B Inhibitor on the Concentration of Intravenously Administered Nalbuphine Material and Methods:

The experiment follows the same protocol as described in the "material and methods" section of "Experiment 3", but an insertion of a catheter tube in the carotid artery was added, in addition to those procedures described in previous "3. Methods" step. Such a design is for the purpose of delivering the drug via the vein while obtaining blood samples from the artery. The insertion of a tube is similar to the step ii in "Experiment 3", but a special attention is necessary to avoid blood loss by clamping the artery near the heart during the insertion of the tubing. Just insert about 2.5 cm into the artery will be enough.

Take 0.3 mL blood sample from the PE-50 catheter, at 15, 20, 30, 45, 60, 90, 120, and 180 minutes after the drug was given to SD rats, and analyze the concentration of nalbuphine in the blood in both the experimental and control sets.

Result:

Table 8 depicts the change of nalbuphine in blood, from the pharmacokinetic point of view. There are obvious differences in AUC, Cmax, CL/F, and V/F between the control and the experimental animals. The highest concentration in blood (Cmax) reaches 365±119 ng/ml, after SD rat was given 100 mg/Kg nalbuphine and 4 mg capillarisin intravenously. While in the control animals, the Cmax is a relatively lower 154±30 ng/ml with only 100 mg/Kg nalbuphine was given.

The above result demonstrates that intravenous capillarisin administration inhibits UCT2B. it increases the nalbuphine concentration to 32.68 times higher than in the control animals, and enhances absolute bio-availability by 2.7±0.4%. In comparison, the oral administration of nalbuphine to SD rats with and without the addition of capillarisin will increase the absolute bio-availabilities to 127.85±36.41% and 12.759±4.64% respectively.

Figure 2:
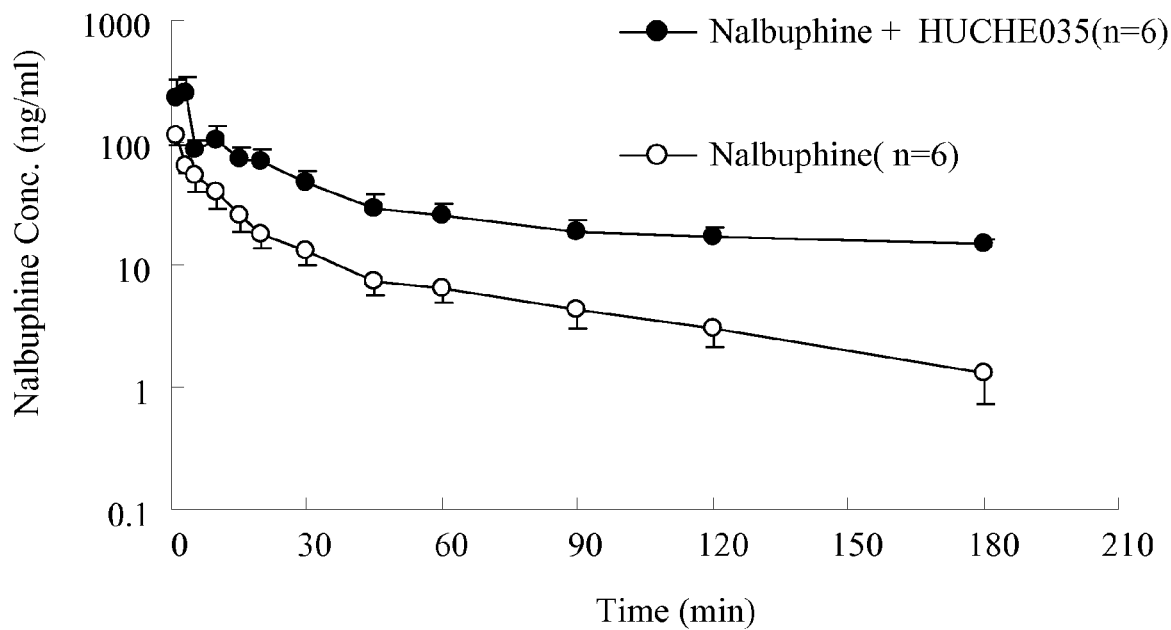
FIG. 2 depicts the temporal effect of capillarisin on the concentration of nalbuphine in blood, after the SD rats were intravenously injected with nalbuphine.
Figure 2:
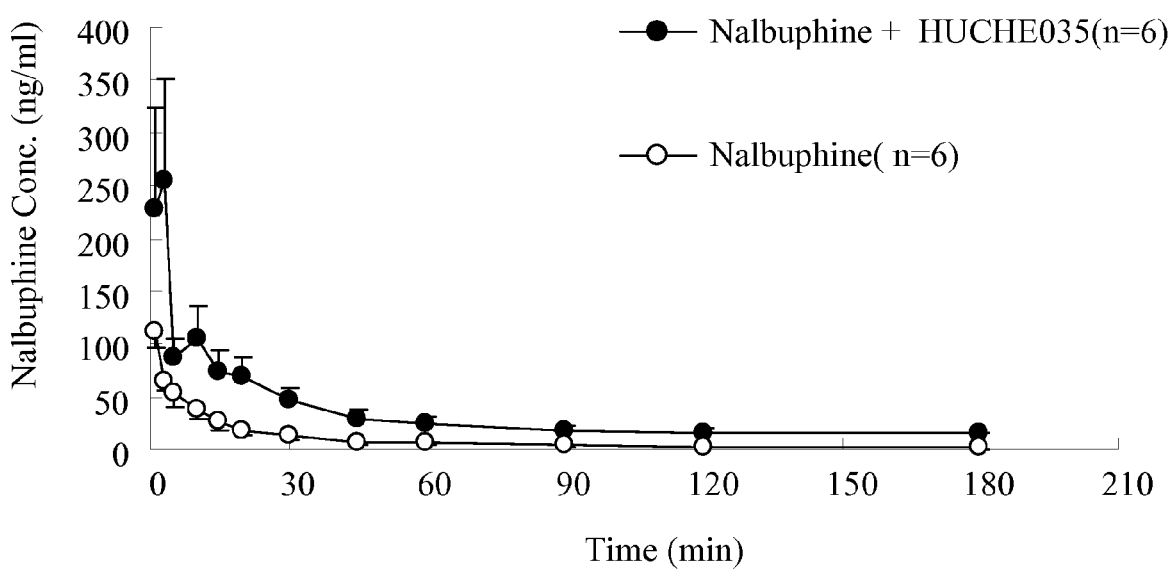

FIG. 2 shows the temporal effect of capillarisin on the concentration of nalbuphine in blood after SD rats were given nalbuphine intravenously.

The difference in the nalbuphine concentration between the control and experimental animals increases gradually by time. After 180 minutes, the serum nalbuphine concentration in the experimental animals was 2.37 times that of the control animals.

TABLE 8

Pharmacokinetic analysis of intravenous administration of nalbuphine without capillarisin (control sets) and with capillarisin (experimental sets)

| PK Parameters | (unit) | Control (n = 6) Nalbuphine (Mean ± SE) | Experiment (n = 6) Nalbuphine + capillarisin (Mean ± SE) |
|---|---|---|---|
| Cmax | (ng/mL) | 154 ± 30 | 365 ± 119 |
| AUC(0-t) | (min * ng/mL) | 1731 ± 295 | 5862 ± 1188** |
| AUC(total) | (min * ng/mL) | 1909 ± 330 | 7135 + 1218** |
| k | (1/min) | 0.016 ± 0.004 | 0.017 ± 0.008 |
| t½ | (min) | 77 ± 29 | 63 ± 11 |
| MRT | (min) | 59 ± 12 | 89 ± 17 |
| CL/F | (mL/min/kg) | 843 ± 235 | 204 ± 34* |
| V/F | (mL/kg) | 42194 ± 6492 | 19379 ± 6475* |

Note:
*indicates < 0.05;
**indicates p ≤ 0.01

EXPERIMENT 5

Comparison of the Effect of UGT2B Inhibitor on the Orally and Intravenously Administered Nalbuphine Concentrations Material and Method:

This experiment uses the same "material and method" as described in Experiments 3 and 4.

Deliver nalbuphine orally and intravenously to control animals, and nalbuphine and capillarisin orally to experimental animals. Take 0.3 ml blood samples from the PE-50 tubing to analyze the concentration of nalbuphine in the serum.

Figure 3:
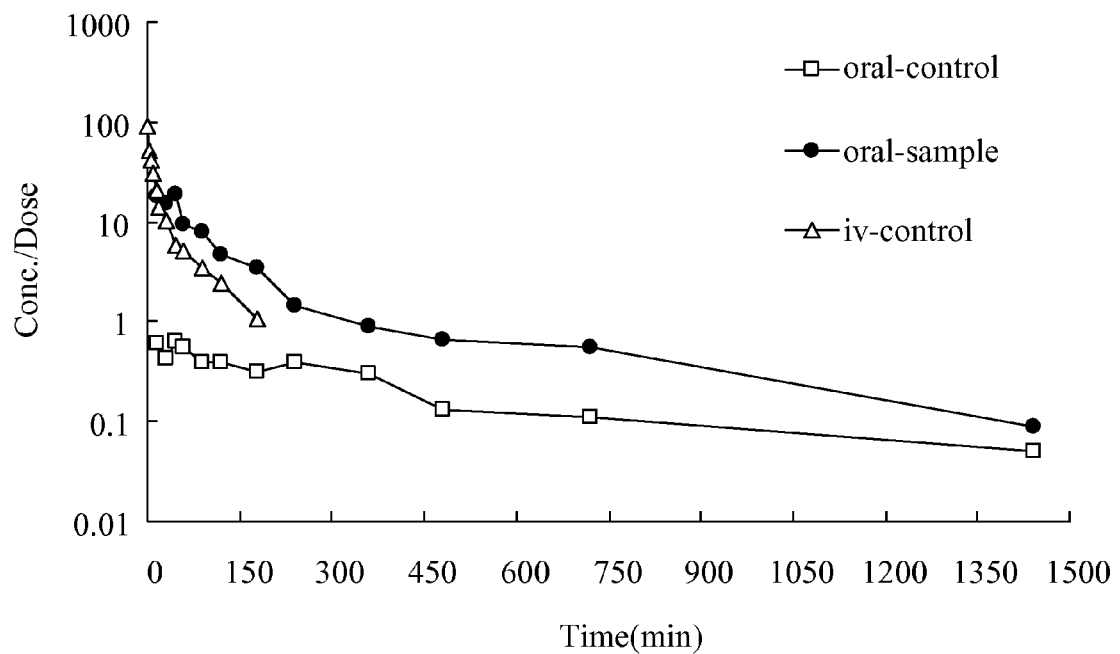
FIG. 3 compares the temporal effect of the concentration of nalbuphine in blood of SD rats between the samples and the controls. The control animals were treated with nalbuphine orally as well as intravenously while the sample animals were treated with nalbuphine and capillarisin.
Figure 3:
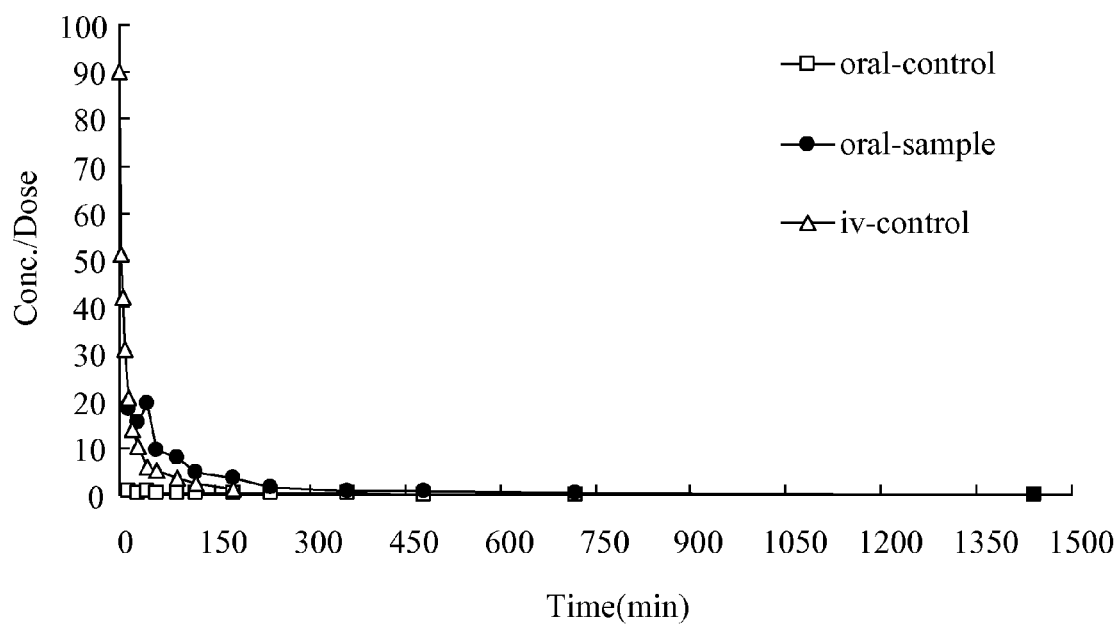

Result:

FIG. 3 shows the changes of the nalbuphine concentration in SD rats at different time, after nalbuphine was orally and intravenously given to the control group while nalbuphine and capillarisin were orally given to the experiment group.

The absorption of orally administered drugs is affected by three factors: adsorption in the gastroenterological tract, first-pass effect, and other metabolism; while the intravenous route is affected mainly by metabolism other than the first-pass effect. Comparing the animals that were orally given inhibitor (experiment group) with those intravenously given drug without inhibitor (control group), as shown in FIG. 3, the oral absorption is significantly improved with the presence of the inhibitor. Its absolute bio-availability increases from 5% to 108%. In addition, the AUC values are similar in both sets of animals, indicating the addition of the inhibitor enhances the oral absorption of nalbuphine. [Note: compare values in Table 5 and 6, the AUC value of orally administered nalbuphine and capillarisinin in Table 5 was 244071±69510, while the AUC value in the control set (intravenous administration) was 7135±1218. They seem to be inconsistent with the above conclusion. The discrepancy is caused by the difference in quantity: when given the nalbuphine through oral route, the dose was 100 mg/Kg, while the intravenous dose was 1 mg/Kg].

Many changes and modifications in the above described embodiment of the invention can, of course, be carried out without departing from the scope thereof. Accordingly, to promote the progress in science and the useful arts, the invention is disclosed and is intended to be limited only by the scope of the appended claims.

What is claimed is:

1. A pharmaceutical composition capable of enhancing clearance rate of morphine-like analgesic agents, including:
    an active ingredient as an Uridine diphosphate (UDP)-glucuronosyltransferases 2B (UGT2B) enhancer with a concentration of 8.5 μM-850 μM that is a compound in a free base form or a pharmaceutically acceptable salt form that is selected from the group consisting of: (+)-epicatechin, (−)-epicatechin, and ergosterol;
    a pharmaceutically effective amount of morphine-like analgesic agent including at least one selected from the group consisting of: (−)-morphine, naloxone, nalorphine, oxymorphone, hydromorphone, dihydromorphone, codeine, naltrexone, nalbuphine and buprenorphine; and
    a pharmaceutically acceptable inert ingredient.

2. A method for enhancing a clearance rate of morphine-like agents in a patient, comprising:
    orally administering a pharmaceutically effective amount of Uridine diphosphate (UDP)-glucuronosyltransferases 2B (UGT2B) enhancers and a pharmaceutically effective amount of morphine-like analgesic agent which is metabolized by UGT2B to said patient in need thereof, wherein said UGT2B enhancer with a concentration of 8.5 μM-850 μM includes at least one selected from the group consisting of: (+)-epicatechin, (−)-epicatechin, and ergosterol; and wherein said morphine-like analgesic agent which is at least one selected from the group consisting of: (−)-morphine, naloxone, nalorphine, oxymorphone, hydromorphone, dihydromorphone, codeine, naltrexone, nalbuphine and buprenorphine.

* * * * *